(12) United States Patent
Reese et al.

(10) Patent No.: US 6,884,881 B1
(45) Date of Patent: Apr. 26, 2005

(54) 2'-SUBSTITUTED RNA PREPARATION

(75) Inventors: Colin Bernard Reese, London (GB); Quanlai Song, San Marcos, CA (US)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 09/914,596

(22) PCT Filed: Mar. 15, 2000

(86) PCT No.: PCT/GB00/00965

§ 371 (c)(1),
(2), (4) Date: Dec. 5, 2001

(87) PCT Pub. No.: WO00/56747

PCT Pub. Date: Sep. 28, 2000

(30) Foreign Application Priority Data

Mar. 19, 1999 (GB) .............................................. 9906328

(51) Int. Cl.[7] .................. C07H 19/00; C07H 19/048
(52) U.S. Cl. ................... 536/28.1; 536/22.1; 536/23.1; 536/25.3; 536/27.1; 536/27.11
(58) Field of Search .............................. 536/22.1, 23.1, 536/25.3, 27.1, 27.11, 28.1, 28.2, 28.53, 27.12, 27.14, 25.31, 25.32, 25.33, 25.34, 26.7, 26.8, 4.1

(56) References Cited

FOREIGN PATENT DOCUMENTS

| WO | WO 95/35102 | 12/1995 |
|---|---|---|
| WO | WO 96/27606 | 9/1996 |

OTHER PUBLICATIONS

McGee D P C et al: "Reaction of Anhydronucleosides with Magnesium Alkoxides: Regiospecific Synthesis of 2'–0–Alkylpyrimidine Nucleosides" Nucleosides & Nucleotides, US, Marcel Dekker, Inc., vol. 15, No. 11/12, Jan. 1, 1996, pp. 1797–1803, XP002066801 ISSN: 0732–8311 abstract.

B.S. Ross et al.: "A Novel and Economical Synthesis of 2'–0–Alkyl–Uridines." Nucleosides & Nucleotides., vol. 16, No. 7–9, 1997, pp. 1641–1643, XP002137095 Marcel Dekker, Inc., US, ISSN: 0732–8311 the whole document.

*Primary Examiner*—James O. Wilson
*Assistant Examiner*—Patrick Lewis
(74) *Attorney, Agent, or Firm*—Pillsbury Winthrop LLP

(57) ABSTRACT

A process for the preparation of a compound of formula (1):

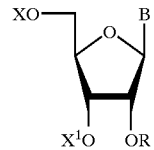

is provided, which comprises the reaction a compound of formula (2):

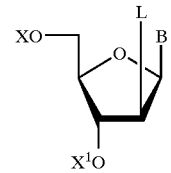

with a compound of formula $Al(OR)_3$ under substantially anhydrous conditions. X, and $X^1$ are each independently H or a protecting group, B is a base; R is an alkyl, alkoxyalkyl, alkenyl or alkynyl group, each of which may be optionally substituted, and L is a leaving group.

14 Claims, No Drawings

2'-SUBSTITUTED RNA PREPARATION

This application is the National Phase of International Application PCT/GB00/00965 filed Mar. 15, 2000 which designated the U.S. and that International Application was published under PCT article 21(2) in English.

The present invention relates to a process for preparing 2'-O-substituted nucleosides, and more particularly to a process for the preparation of 2'-O-substituted uridine and cytidine.

The possibility that synthetic oligonucleotides might be effective inhibitors of gene expression and be used as chemotherapeutic agents has stimulated much research work in recent years. In order to avoid their degradation by cellular nucleases, it is essential that such oligonucleotides should be modified. Modifications can be made to the internucleotide linkages, the base residues and the sugar residues. A large number of oligonucleotide analogues in which the internucleotide linkages have been modified, especially as phosphorothioates with non-bridging sulphur atoms, have been described. Several of these phosphorothioate analogues are promising drug candidates that are now undergoing clinical trials. However, phosphorothioates do have some disadvantages. Thus, they do not display optimal RNA-binding properties and they also have a tendency to bind to proteins in a non-specific manner. Possible base modifications are clearly limited as they must not lead to a significant decrease in hybridisation properties. Recently, considerable interest has been directed towards the modification of the sugar residues. One particular type of modification involves the introduction of 2'-α-alkoxy groups (as in 2'-O-alkyl-oligoribonucleotides). While, in general, small alkoxy groups (such as methoxy) promote better hybridisation properties with complementary ribonucleic acids (RNA), nuclease resistance tends to increase with an increase in the size of the alkoxy group. 2-Methoxyethoxy has emerged as an alkoxy group that confers both good hybridisation properties and high nuclease resistance. It therefore seems likely that 2'-O-(2-methoxyethyl)-ribonucleosides will be incorporated into a second generation of potential oligonucleotide chemotherapeutic agents. For this reason, the development of convenient methods for the preparation of 2'-O-(2-methoxyethyl)-ribonucleosides has become a matter of much importance.

The preparation of 2'-O-(2-methoxyethyl)-ribonucleosides, starting from D-ribose, has previously been described. These preparations involved the use of protecting groups and required a relatively large number of steps. For example, 2'-O-(2-methoxyethyl)-5-methyluridine was prepared by Martin, P. Helv. Chim. Acta 1995, 78, 486–504 from D-ribose in 10 steps and in 33% overall yield. A later report by McGee and Zhai in Abstracts of American Chemical Society National Meeting, Division of Organic Chemistry, March 1996 paper 253 revealed a much more convenient procedure for the preparation of 2'-O-alkyl derivatives of the main pyrimidine ribonucleosides. Thus, when 5'-O-(4,4'-dimethoxytrityl)2,2'-anhydro-1-β-D-arabinofuranosyluracil was heated with magnesium methoxide in N,N-dimethylformamide (DMF) at 100° C., 5'-O-(4,4'-dimethoxytrityl)-2'-O-methyluridine was obtained in 94% yield. Somewhat lower yields of the corresponding 5'O-ethyl-, 5'-O-(n-propyl)- and 5'-O-allyl-uridine derivatives were obtained in the reactions between the same substrate and the appropriate magnesium alkoxides. It was also reported that magnesium alkoxides could be replaced by calcium alkoxides.

Ross et al reported in Nucleosides and Nucleotides, 1997, 16, 1641–3 that when unprotected 2,2'-anhydro-1-β-D-arabinofuranosyluracil was heated with a twofold excess of trimethyl borate and a stoichiometric quantity of trimethyl orthoformate in methanol at 150° C., under pressure, for 42 h, 2'-O-methyluridine was obtained in 86% isolated yield. 2'-O-Methyl-5-methyluridine was similarly prepared from 2,2'-anhydro-5-methyl-(1-β-D-arabinofuranosyluracil) by the borate ester procedure and, although no experimental details were provided, the preparation of 2'-O-methylcytidine was also reported. The yield of 2'-O-alkyl-uridine was stated to decrease with increasing alcohol size.

It remains desirable to identify additional or alternative routes for the preparation of 2'-O-substituted nucleosides.

According to the present invention, there is provided a process for the preparation of a compound of formula (1):

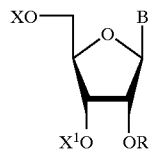

wherein:
X, and $X^1$ are each independently H or a protecting group;
B is a base; and
R is an alkyl, alkoxyalkyl, alkenyl, or alkynyl group, each of which may be optionally substituted;
which comprises reacting a compound of formula (2):

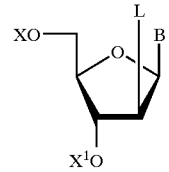

wherein
L is a leaving group; and
B, X and $X^1$ are as defined above
with a compound of formula $Al(OR)_3$ wherein R is as defined above, under substantially anhydrous conditions.

When R is alkenyl, the alkenyl group is often a $C_{1-4}$ alkenyl group, especially an allyl or crotyl group. When R represents alkyl, the alkyl group is preferably a $C_{1-4}$ alkyl, and most preferably a methyl or ethyl group. When R represents alkoxyalkyl, the alkoxyalkyl group is often a $C_{1-4}$ alkyoxy$C_{1-4}$ alkyl group, and preferably a methoxyethyl group. When R is alkynyl, the alkynyl group is often a $C_{1-4}$ alkynyl group, especially a propargyl group. The alkyl, alkenyl, alkynyl and alkoxyalkyl groups may themselves be substituted by one or more substituents, particularly halogen, especially F, Cl or Br, and amino substituents.

Examples of protecting groups which can be represented by X and $X^1$ include acid labile protecting groups, particularly trityl and substituted trityl groups such as dimethoxytrityl and 9-phenylxanthen-9-yl groups; acid-labile acetal protecting groups, particularly 1-(2-fluorophenyl)-4-methoxypiperidine-4-yl (Fpmp); and base labile-protecting groups such as acyl groups, commonly comprising up to 16 carbon atoms, such as ethanoyl groups or fatty alkanoyl groups, including particularly linear or branched $C_{6-16}$ alkanoyl groups, such as lauroyl groups; benzoyl and substituted benzoyl groups, such as alkyl, commonly $C_{1-4}$ alkyl-, and halo, commonly chloro or fluoro, substituted benzoyl groups.

Other suitable protecting groups include those derived from gamma keto acids, such as levulinoyl groups and substituted levulinoyl groups. Substituted levulinoyl groups include 5-halo-levulinoyl, such as 5,5,5-trifluorolevulinoyl and benzoylpropionyl groups; and silyl and siloxane ethers, such as alkyl, commonly $C_{1-4}$, alkyl, and aryl, commonly phenyl, silyl ethers, particularly trialkylsilyl groups, often tri($C_{1-4}$-alkyl)silyl groups, such as tertiary butyl dimethyl silyl and tertiary butyl diphenyl silyl groups.

Bases which can be represented by B include nucleobases, particularly purines, especially adenine (A) and guanine (G); and pyrimidines, especially thymine M, cytosine (C), and uracil (U); and substituted derivatives thereof. Examples of substituents which may substitute the bases, in addition to protecting groups, include alkyl, especially $C_{1-4}$-alkyl, particularly methyl; halogen, particularly Cl or Br; amino; alkenyl, especially $C_{1-4}$-alkenyl and particularly allyl; alkoxyalkyl, especially $C_{1-4}$alkoxy$C_{1-4}$alkyl, particularly methoxyalkyl; and alkynyl, particularly propargyl, substitutents. The alkyl, alkenyl, alkynyl and alkoxyalkyl groups may themselves be substituted by one or more substituents, particularly halogen, especially F, Cl or Br, and amino substituents.

In addition to the presence of protecting groups X and $X^1$, bases employed in present invention may also be protected where necessary by suitable protecting groups. Protecting groups employed are those known in the art for protecting such bases. For example, A and/or C can be protected by benzoyl, including substituted benzoyl, for example alkyl- or alkoxy-, often $C_{1-4}$ alkyl- or $C_{1-4}$alkoxy-, benzoyl; pivaloyl; and amidine, particularly dialkylaminomethylene, preferably di($C_{1-4}$-alkyl) aminomethylene such as dimethyl or dibutyl aminomethylene. G may be protected by a phenyl group, including substituted phenyl, for example 2,5-dichlorophenyl and also by an isobutyryl group. T and U generally are not protected, but in certain embodiments they may advantageously be protected, for example at O4 by a phenyl group, including substituted phenyl, for example 2,4-dimethylphenyl or at N3 by a pivaloyloxymethyl, benzoyl, alkyl or alkoxy substituted benzoyl, such as $C_{1-4}$ alkyl- or $C_{1-4}$ alkoxybenzoyl.

In certain embodiments, X and $X^1$ comprise a single protecting group which protects both the 3' and 5' positions. Examples of such groups include disiloxanes, especially tetraalkyldisiloxanes, such as tetraisopropyldisiloxane.

Leaving groups which can be represented by L include those leaving groups which can be displaced by a nucleophile of formula $RO^-$. Examples of preferred leaving groups include groups of formula $—OSO_2CH_3$, $—OSO_2CF_3$, Cl, Br, I, O-Mesyl, O-Brosyl and O-Tosyl groups.

In certain preferred embodiments, the leaving group comprises the base, B, chemically bonded to the 2'-position, commonly via an oxygen or sulphur atom or a group of formula $—NR^X—$, wherein $R^X$ is H or a $C_{1-6}$ alkyl or aryl, such as a phenyl, group. Most preferably, the base is uracil bonded to the 2'-position via an oxygen atom.

Accordingly, a second aspect of the present invention provides a process for the preparation of a compound of formula (3):

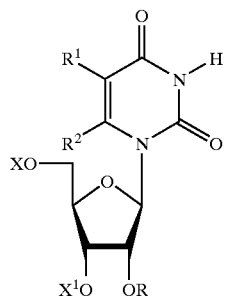

wherein:
X and $X^1$ are as defined above;
$R^1$ and $R^2$ are each independently H, alkyl, alkenyl, alkynyl, or halogen; and R is an alkyl, alkoxyalkyl, alkenyl, or alkynyl group, each of which may be optionally substituted;
which comprises the reaction of a compound of formula (4)

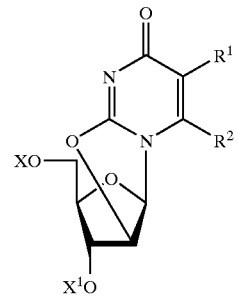

wherein
X, $X^1$, $R^1$ and $R^2$ are as defined above;
with a compound of formula $Al(OR)_3$ wherein R is as defined above, under substantially anhydrous conditions.

When either of $R^1$ and $R^2$ is alkenyl, the alkenyl group is often a $C_{1-4}$ alkenyl group, especially an allyl or crotyl group. When either of $R^1$ and $R^2$ represents alkyl, the alkyl group is preferably a $C_{1-4}$ alkyl, and most preferably a methyl or ethyl group. When either of $R^1$ and $R^2$ represents alkoxyalkyl, the alkoxyalkyl group is often a $C_{1-4}$ alkyoxy$C_{1-4}$ alkyl group, and preferably a methoxyethyl group. When either of $R^1$ and $R^2$ is alkynyl, the alkynyl group is often a $C_{1-4}$ alkynyl group, especially a propargyl group. The alkyl, alkenyl and alkynyl groups represented by $R^1$ or $R^2$ may be substituted by one or more substituents, particularly halogen, especially F, Cl or Br, and amino substituents. When either of $R^1$ and $R^2$ is halogen the halogen is preferably Cl, Br or I. Most preferably, both of $R^1$ and $R^2$ represent H, or $R^1$ represents $C_{1-4}$ alkyl and $R^2$ represents H.

The process according to the present invention takes place in the presence of a suitable substantially anhydrous solvent. Examples of suitable solvents include halocarbons such as chloroform, 1,2-dichloroethane and chlorobenzene; esters, particularly alkyl esters such as ethyl acetate, and methyl or ethyl propionate; amides such as N-methylpyrrolidinone, dimethylformamide and particularly dimethylacetamide; lower alkyl, for example $C_{2-4}$ nitriles such as acetonitrile; ethers such as glyme and diglyme and cyclic ethers such as tetrahydrofuran and dioxane; tertiary amines, such as N-methylpyrrolidine and heterocyclic aromatic amines such as pyridine. and alcohols, most commonly the alcohol corresponding to the group R, for example methanol, ethanol, methoxyethanol, allyl alcohol or propargyl alcohol.

The process of the present invention is often carried out at a temperature of from room temperature, such as about 25° C., up to the reflux temperature of the solvent employed. Temperatures above the normal boiling point of the solvent employed can be employed if desired by carrying out the process under super-atmospheric pressure conditions, for example in a sealed reaction vessel. Commonly, the temperature is in the range of from 50 to 150° C.

The process commonly takes place over a period ranging from several hours, for example from 4 to 12 hours, to several days, for example from 1 to 2 days, depending on the reagents and reaction conditions employed.

When the compound of formula (1) comprises the base uracil, the uracil moiety may be converted to a cytosine moiety. Similarly, the uracil moiety comprised in the compound of formula (3) may also be converted to a cytosine moiety. The skilled man will recognise that a number of different techniques can be employed. Examples of such techniques include:

a) the nitrophenyl route (see Miah et al, Nucleosides and Nucletides, 1997, 16, pp 53–65) where for example the uracil containing compound is reacted with chlorotrimethylsilane in acetonitrile/1-methylpyrrolidine, then with trifluoroacetic anhydride, followed by 4-nitrophenol. The 4-nitrophenol moiety is then displaced with ammonia in aqueous dioxane to yield the cytosine-containing compound; and
b) the triazolation procedure, (see Divakar et al, J. Chem. Soc. Perkin Trans. 1, 1982, 1171–6) where for example the uracil containing compound is reacted with acetic anhydride in pyridine, then, after work up, with phosphoryl chloride, 1,2,4-triazole and triethylamine in acetonitrile to give the 4-triazolopyrimidine. The triazole moiety is then displaced with ammonia in aqueous dioxane, and acetyl groups removed to yield the cytosine-containing compound.

Protecting groups can be removed using methods known in the art for the particular protecting group and function. For example, acyl protecting groups, such as ethanoyl and benzoyl groups, can be removed by treatment with a solution of ammonia in an alcohol such as ethanol.

Benzoyl, pivaloyl and amidine groups can be removed by treatment with concentrated aqueous ammonia.

Trityl groups present can be removed by treatment with acid, for example a solution of dichloroacetic acid in dichloromethane. With regard to the overall unblocking strategy an important consideration is that the removal of trityl, often DMTr, protecting groups ('detritylation') should proceed without concomitant depurination when base B represents a purine, especially adenine. Such depurination can be suppressed by effecting 'detritylation' with a dilute solution of hydrogen chloride at low temperature, particularly ca. 0.45 M hydrogen chloride in dioxane-dichloromethane (1:8 v/v) solution at −50° C. Under these reaction conditions, 'detritylation' can be completed rapidly, and in certain cases after 5 minutes or less.

Silyl protecting groups may be removed by fluoride treatment, for example with a solution of a tetraalkyl ammonium fluoride salt such as tetrabutyl ammonium fluoride.

Fpmp protecting groups may be removed by acidic hydrolysis under mild conditions.

Compounds produced by the present invention may be incorporated in the assembly of a desired oligonucleotide by coupling with other nucleosides or oligonucleotides (which may themselves have been prepared using the present invention) and such a process forms a further aspect of the present invention. The coupling processes employed are those known in the art for the preparation of oligonucleotides.

The present invention is further illustrated, but not limited by, the following Examples.

GENERAL EXPERIMENTAL DETAILS

Mps are uncorrected. $^1$H and $^{13}$C NMR spectra were measured at 360.1 and 90.6 MHz respectively, with a Bruker AM 360 spectrometer; tetramethylsilane was used as an internal standard. TLC was carried out with Merck silica gel 60 $F_{254}$ pre-coated plates (Art 5715), which were developed in solvent system A [CHCl$_3$-MeOH (85:15 v/v)]. Short column chromatography was carried out on silica gel (Merck Art 7729). Acetonitrile and 1-methylpyrrolidine were dried by heating, under reflux, with calcium hydride and were then distilled. N,N-Dimethylacetamide (DMA) was dried by distillation over calcium hydride under reduced pressure. 2-Methoxyethanol was dried by heating with aluminium foil (1 g/250 ml), under reflux, and was then distilled. Diethyl ether was dried over sodium wire.

Preparation of 2,2'-Anhydro-1-β-D-arabinofuranosyluracil

Uridine (12.21 g, 50 mmol), diphenyl carbonate (11.79 g, 55 mmol), sodium hydrogen carbonate (0.219, 2.5 mmol) and dry DMA (10 ml) were heated together, with stirring, at 100° C. After 5 h, the products were cooled to room temperature, and diethyl ether (100 ml) was added with stirring. After 2 hours, the colourless precipitate (11.70 g) was collected by filtration and was washed with ether (2×50 ml). The sole nucleoside constituent of the precipitated material was identified as 2,2'-anhydro-1-β-D-arabinofuranosyluracil (calculated quantitative yield, 11.31 g) by comparison with authentic material.

Preparation of 2'-O-(2-Methoxyethyl)uridine

Aluminium foil (3.64 g, 0.135 mol) and dry 2-methoxyethanol (135 ml) were heated, under reflux, for ca. 1 hr until all of the aluminium had been consumed. Crude (see above) 2,2'-anhydro-1-β-D-arabinofuranosyluracil (10.18 g, ca. 43.5 mmol) was added and the reactants were heated, under reflux, for 48 hours. Absolute ethanol (200 ml), followed by water (7.3 ml, 0.405 mol) and Celite were added to the cooled products. The resulting mixture was heated, under reflux, for 10 minutes and was then filtered. The residue was washed with ethanol (3×100 ml). The combined filtrate and washings were evaporated under reduced pressure to give a pale yellow solid. The material was purified by short column choromatography on silica gel (70 g): the appropriate fractions, which were eluted with dichloromethane-methanol (90:10 v/v), were evaporated under reduced pressure to give the title compound as a colourless solid (12.05 g, ca. 91%).

Preparation of 2'-O-(2-Methoxyethyl)cytidine

2'-O-(2-Methoxyethyl)uridine (6.05 g, 20.0 mmol), 1-methylpyrrolidine (20 ml, 0.192 mol), chlorotrimethylsilane (7.6 ml, 59.9 mmol) and dry acetonitrile (100 ml) were stirred together at room temperature. After 1 hour, the reactants were cooled to 0° C. (ice-water bath) and trifluoroacetic anhydride (7.1 ml, 50.3 mmol) was added dropwise over 5 minutes. After a further period of 30 minutes at 0° C., 4-nitrophenol (8.35 g, 60 mmol) was added to the stirred reactants which were maintained at 0° C. After 3 hours, the products were poured into saturated aqueous sodium hydrogencarbonate (200 ml), and the resulting mixture was extracted with dichloromethane (3×100 ml). The combined organic layers were dried (MgSO$_4$), and evaporated under reduced pressure. Concentrated aqueous ammonia (d 0.88, 20 ml) was added to a stirred solution of the residue in dioxane (100 ml), contained in a sealed flask that was then heated at 55° C. for 24 hours. The resulting yellow solution was concentrated under reduced pressure, and the residue was evaporated with absolute ethanol (3×50 ml). The products were fractionated by short column chromatography on silica gel: the appropriate fractions, which were eluted with dichloromethane-methanol-triethylamine (93:7:0.5 to 90:10:0.5 v/v) were evaporated under the reduced pressure to give the title compound as an off-white solid (5.07 g 84%).

What is claimed is:
1. A process for the preparation of a compound of formula (1):

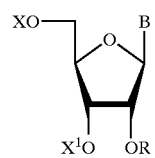

which comprises reacting a compound of formula (2):

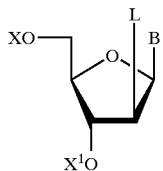

with a compound of formula Al(OR)$_3$, under substantially anhydrous conditions wherein:

X, and X$^1$ are each independently H or a protecting group;

B is a nucleobase; and

R is an alkyl, alkoxyalkyl, alkenyl, or alkynyl group, each of which may be substituted by one or more of halogen or amino substitutes; and L is a leaving group.

2. A process according to claim 1, wherein the leaving group is selected from the group consisting of —OSO$_2$CH$_3$, —OSO$_2$CF$_3$, Cl, Br, I, O-Mesyl, O-Brosyl O-Tosyl and the nucleobase, B, chemically bonded to the 2'-position, via an oxygen or sulphur atom or a moiety of formula —NR$^x$—, wherein R$^x$ is H or a C$_{1-6}$ or an aryl group.

3. A process for the preparation of a compound of formula (3):

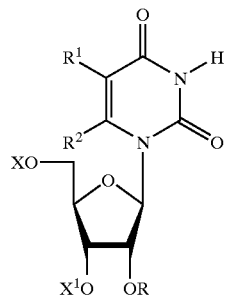

which comprises reacting a compound of formula (4)

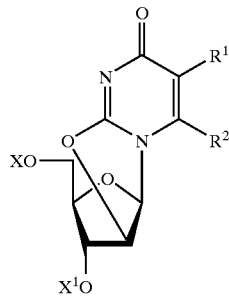

with a compound of formula Al(OR)$_3$, under substantially anhydrous conditions wherein:

X, and X$^1$ are each independently H or a protecting group;

R$^1$ and R$^2$ are each independently H, alkyl, alkenyl, alkynyl, or halogen; and R is an alkyl alkoxyalkyl, alkenyl, or alkynyl group, each of which may be unsubstituted or substituted by one or more of halogen or amino substituents.

4. A process according to claim 3, wherein R$^1$ and R$^2$ are both K or R$^1$ is C$_{1-4}$ alkyl, and R$^2$ is H.

5. A process according to claim 1 or claim 3, wherein R is a C$_{1-4}$ alkenyl group, a C$_{1-4}$ alkyl group, a C$_{1-4}$ alkyoxyC$_{1-4}$ alkyl group or a C$_{1-4}$ alkyl group.

6. A process according to claim 5, wherein R is a methoxyethyl group.

7. A process according to claim 1 for the preparation of a compound of Formula (1) wherein B represents cytosine, or a substituted derivative thereof, which comprises:

a) preparing said compound of Formula (1) wherein B represents uracil, or a substituted derivative thereof; and b) converting the uracil moiety to the equivalent cytosine moiety.

8. A process for the preparation of a compound of Formula (1)

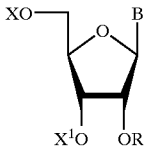

wherein X and X$^1$ are each, independently, H or a protecting group;

R is an alkyl, alkoxyalkyl, alkenyl, or alkynyl group, each of which may be unsubstituted or substituted by one or more of halogen or amino substituents; and B represents cytosine, or a substituted derivative thereof; which comprises a) preparing a compound of formula (3), by a process according to claim 3; and b) converting the uracil moiety to the equivalent cytosine moiety.

9. A process for the preparation of a product oligonucleotide which comprises the coupling to a nucleoside or an oligonucleotide of a compound prepared by a process according to any one of claim 1, 3, 7 or 8.

10. A process according to claim 1 or claim 3, wherein X and X$^1$ each represent H.

11. A process according to claim 1 or claim 3, wherein at least one of X and X$^1$ represent said protecting group.

12. A process according to claim 11, wherein the protecting group or groups are selected from the group consisting of acid labile protecting groups, acid-labile acetal protecting groups; and base labile-protecting groups.

13. A process according to claim 1, wherein the leaving group L is selected from the group consisting of —OSO$_2$CH$_3$, —OSO$_2$CF$_3$, Cl, Br, I, O-Mesyl, O-Brosyl, and O-Tosyl.

14. A process according to claim 1, wherein the leaving group L is pyrimidine.

* * * * *